US008383170B2

(12) United States Patent
Loewy et al.

(10) Patent No.: US 8,383,170 B2
(45) Date of Patent: Feb. 26, 2013

(54) MUCOSAL FORMULATION

(75) Inventors: Zvi G. Loewy, Fair Lawn, NJ (US); William Zev Levine, Jerusalem (IL); Aron J. Saffer, Bet Shemesh (IL)

(73) Assignee: Izun Pharmaceuticals Corporation, New York, NY (US)

( * ) Notice: Subject to any disclaimer, the term of this patent is extended or adjusted under 35 U.S.C. 154(b) by 0 days.

(21) Appl. No.: 13/291,670

(22) Filed: Nov. 8, 2011

(65) Prior Publication Data

US 2012/0082738 A1    Apr. 5, 2012

Related U.S. Application Data

(63) Continuation of application No. 11/780,593, filed on Jul. 20, 2007, now Pat. No. 8,075,924.

(60) Provisional application No. 60/807,846, filed on Jul. 20, 2006.

(51) Int. Cl.
*A01N 65/00* (2009.01)
*A61K 36/28* (2006.01)
*A61P 1/02* (2006.01)
*A61P 31/00* (2006.01)

(52) U.S. Cl. .................. 424/725; 424/737; 514/902

(58) Field of Classification Search .................. None
See application file for complete search history.

(56) References Cited

U.S. PATENT DOCUMENTS

| | | | |
|---|---|---|---|
| 5,900,247 A | 5/1999 | Rault et al. |
| 5,906,810 A | 5/1999 | Turner |
| 6,348,503 B1 | 2/2002 | Squires |
| 6,355,229 B1 | 3/2002 | Adamy |
| 6,355,684 B1 | 3/2002 | Squires |
| 6,576,267 B2 | 6/2003 | Gelber et al. |
| 7,008,628 B2 | 3/2006 | Ron et al. |
| 7,033,606 B1 | 4/2006 | Besse et al. |
| 7,285,295 B2 | 10/2007 | Levine et al. |
| 2003/0003140 A1 | 1/2003 | Domb et al. |
| 2004/0151789 A1 | 8/2004 | Levine et al. |
| 2005/0100612 A1 | 5/2005 | Capps |
| 2006/0193790 A1 | 8/2006 | Doyle et al. |
| 2007/0053849 A1 | 3/2007 | Doyle et al. |
| 2007/0292487 A1 | 12/2007 | Loewy et al. |
| 2008/0020027 A1 | 1/2008 | Loewy et al. |

FOREIGN PATENT DOCUMENTS

| | | |
|---|---|---|
| EP | 0846467 A1 | 5/1997 |
| EP | 1236466 A1 | 4/2002 |
| JP | 07010722 A | 1/1995 |
| WO | 9745134 A1 | 12/1997 |
| WO | 02094300 A1 | 11/2002 |
| WO | 02100424 A1 | 12/2002 |
| WO | 2004047813 A1 | 6/2004 |

OTHER PUBLICATIONS

International Search Report and Written Opinion mailed Feb. 10, 2008 for PCT US2007/073962.
International Preliminary Report on Patentability mailed Jan. 29, 2009 for PCT US2007/073962.
Thompson, KD Antiviral Research (1998). 39:55-61. Antiviral activity of Viracea against acylovir susceptible and acylovir resistant strains of herpes simplex virus.
Kawabata, S et al,. J. Med. Microbiol (1993); 38: 54-60. Effects of selected surfactants on purified glucosyltransferases from mutans streptococci and cellular adherence to smooth surfaces.
Jacques, N et al Journal of General Microbiology (1985); 131: 67-72. Does an increase in membrane unsaturated fatty acids account for Tween 80 stimuklation of glucosyltransferase secretion by *Streptococcus salivarius*.
http://www.yourdentistryguide.com/oral-rinse. "Oral Rinses:Mouthrinses and Mouthwashes" authored by Nayda Rondon. Downloaded Feb. 22, 2010.

*Primary Examiner* — Michele Flood
(74) *Attorney, Agent, or Firm* — Moser Taboada

(57) ABSTRACT

Provided, among other things, is a method of treating or ameliorating an indication of mucosal or adjacent tissue comprising periodically applying to mucosa at or adjacent to disease affected tissue a rinse comprising: an effective amount of appropriate composition of herbal bioactive comprising active(s) of one or more of *Sambucus nigra*, *Centella asiatica* or *Echinacea purpurea*; an antimicrobially effective amount of a quaternary ammonium surfactant; and optionally a polymer or mixture of polymers effective to coat said tissue and entrap said extract(s).

11 Claims, No Drawings

MUCOSAL FORMULATION

This application is a continuation of U.S. patent application Ser. No. 11/780,593 filed Jul. 20, 2007 which in turn claims priority to U.S. patent application 60/807,846 filed Jul. 20, 2006. The aforementioned related patent applications are herein incorporated by reference in their entirety.

The present invention relates to an anti-inflammatory oral coating that is applied as a rinse.

Certain herbal extracts have been clinically shown to be effective in treating or ameliorating certain conditions of the mouth. Described in WO 02/094300 and PCT/US05/42348 [corresponding to U.S. Ser. No. 11/284,078, filed 21 Nov. 2005] are a number of useful combinations of herbal extracts for treating or ameliorating diseases of mucosa, and dosage forms for delivering the extracts to discrete regions of the mouth. For example, such combinations, in the delivery form described in PCT/US05/42348, have achieved, in an 80 patient trial, an average of 50% pain reduction in the first ½ hour. In the same trial, average lesion reductions of 40% were achieved in 4 hours.

The delivery devices described in the above-cited documents can be very effective, particularly with discrete lesions. However, in some cases of oral or other mucosal disease the number of lesions can make it at best awkward to apply medicament delivery devices to each of the lesions. Or, the lesions can be located in positions that may make it physically difficult or impossible to deliver a medicament delivery device to the lesions.

Provided herein is a rinse that provides a medicament-delivery coating to the soft tissue surfaces of the mouth, or to other mucosal tissues.

SUMMARY OF THE INVENTION

Provided, among other things, is a method of treating or ameliorating an indication of mucosal or adjacent tissue comprising periodically applying to mucosa at or adjacent to disease affected tissue a rinse comprising: an effective amount of appropriate composition of herbal bioactive comprising active(s) of one or more of *Sambucus nigra, Centella asiatica* or *Echinacea purpurea*; an antimicrobially effective amount of a quaternary ammonium surfactant; and optionally a polymer or mixture of polymers effective to coat said tissue and entrap said extract(s). The method can include, in some embodiments, applying to a portion of the mucosa a film, patch or an adhesive solid formulation comprising appropriate composition of herbal bioactive comprising active(s) of one or more of *Sambucus nigra, Centella asiatica* or *Echinacea purpurea*. The method can be used for treating or ameliorating mucositis secondary to chemotherapy.

The invention further provides a transmucosal delivery rinse comprising: an effective amount of appropriate composition of plant extract(s) comprising herbal bioactive comprising active(s) of one or more of *Sambucus nigra, Centella asiatica* or *Echinacea purpurea*; an antimicrobially effective amount of a quaternary ammonium surfactant, and optionally a polymer or mixture of polymers effective to coat mucosal tissue and entrap said extract(s).

Further provides is a kit for the treatment of an indication of the mucosa or adjacent tissue comprising: transmucosal delivery rinse comprising (i) an effective amount of appropriate composition of herbal bioactive comprising active(s) of one or more of *Sambucus nigra, Centella asiatica* or *Echinacea purpurea* and (ii) polymer or mixture of polymers effective to coat said tissue and entrap said extract(s); and a film, patch or an adhesive solid formulation comprising appropriate composition of plant extract(s) comprising herbal bioactive comprising active(s) of *Sambucus nigra*.

DETAILED DESCRIPTION OF THE INVENTION

1. Plant Extracts

Appropriate plant extract compositions for use in the device include extract of *Sambucus nigra* (SN), and/or plant extracts of *Allium sativum* (AS), *Calendula officinalis* (CO), *Camellia sinensis* (CS), *Centella asiatica* (CA, also known as Gotu Kola), *Commiphora molmol* (CM), *Echinacea purpurea* (EP), *Gaultheria procumbens* (GP), *Hypericum perforatum* (HP), *Krameria triandra* (KT), *Ligusticum porterii-osha* (LP), *Matricaria recutita, Melissa officinalis, Salix alba, Thymus vulgaris, Uncaria tomentosa, Usnea barbata* or *Vaccinium myrtillus*. The extract compositions can include, for example, *Sambucus nigra* extract in an amount from one of the lower percentages (by weight) recited in the next sentence to 90, 95, 96, 97, 98, 99 or 100%. These lower percentages are 50, 55, 60, 65, 70, 75, 80, 85, 90 or 95%. If a second or third extract is present, it may be present, for example in amount from one of the lower percentages to one of the higher percentages recited in the following sentences. Lower percentages for the second or third extracts can be, for example, 0.5, 1, 2, 5, 10 or 20%. Higher percentages can be, for example, 1, 2, 5, 10, 20, 30, 40 or 50%. These ranges, and any other ranges described in this application, can include or exclude one or both endpoints.

The term "extract" is used herein to include all of the many types of preparations containing an effective amount of active ingredients. Thus, the extracts can be produced by cold extraction techniques using a variety of different extraction solvents including, but not limited to, water, fatty solvents (such as olive oil), and alcoholic solvents (e. g. 70% ethanol). Cold extraction techniques are typically applied to softer parts of the plant such as leaves and flowers, or in cases wherein the desired active components of the plant are heat labile. Alternatively, hot extraction techniques, where such solvents are heated to a temperature above room temperature, can be used with the precise value of said temperature being dependent on factors such as the properties of the chosen solvent and extraction efficacy. Hot extraction techniques are more commonly applied to the harder, tougher parts of the plant, such as bark, woody branches and larger roots. In some cases, sequential extractions need to be performed in more than one solvent, and at different temperatures. Standard procedures for producing plant extracts (including hot extraction, cold extraction and other techniques) are described in many publications including "Medicinal plants: a field guide to the medicinal plants of the Land of Israel" (in Hebrew), author: N. Krispil, Har Gilo, Israel, 1986 and "Making plant medicine", author: R. Cech, pub. by Horizon Herbs, 2000.

Exemplary extract compositions by weight percentage include:

| Plant Extract | Composition: | | | | | | | | | | | |
|---|---|---|---|---|---|---|---|---|---|---|---|---|
| | C1 | C2 | C3 | C4 | C5 | C6 | C7 | C8 | C9 | C10 | C11 | C12 |
| SN | 70 | 80 | 90 | 70 | 80 | 90 | | | | | | |
| AS | 30 | 20 | 10 | | | | | | | | | |

-continued

|    | | | | | | | | | | | |
|----|---|---|---|---|---|---|---|---|---|---|---|
| CO | | | | 30 | 20 | 10 | | | | | |
| CA | | | | | | | 30 | 20 | 10 | | | |
| CM | | | | | | | | | | 30 | 20 | 10 |

|    | C13 | C14 | C15 | C16 | C17 | C18 | C19 | C20 | C21 | C22 | C23 | C24 |
|----|-----|-----|-----|-----|-----|-----|-----|-----|-----|-----|-----|-----|
| SN | 70 | 70 | 70 | 70 | 70 | 70 | 70 | 70 | 70 | 70 | 70 | 70 |
| AS | 20 | 20 | 20 | 20 | 20 | | | | | | | |
| CO | 10 | | | | | | 20 | 20 | 20 | | | |
| CA | | 10 | | | | | 10 | | | 20 | 20 | 20 |
| CM | | | 10 | | | | | 10 | | | | |
| EP | | | | 10 | | | | | 10 | | 10 | |
| GP | | | | | 10 | | | | | 10 | | 10 |

|    | C25 | C26 | C27 | C28 | C29 | C30 | C31 | C32 | C33 | C34 | C35 | C36 |
|----|-----|-----|-----|-----|-----|-----|-----|-----|-----|-----|-----|-----|
| SN | 80 | 80 | 80 | 80 | 80 | 80 | 80 | 80 | 80 | 80 | 80 | 80 |
| AS | 10 | 10 | 10 | 10 | 10 | | | | | | | |
| CO | 10 | | | | | | 10 | 10 | 10 | 10 | | | |
| CA | | 10 | | | | | 10 | | | 10 | 10 | 10 |
| CM | | | 10 | | | | | 10 | | | 10 | | |
| EP | | | | 10 | | | | | 10 | | 10 | |
| GP | | | | | 10 | | | | | 10 | | 10 |

|    | C37 | C38 | C39 | C40 | C41 | C42 | C44 | C45 | C46 | C47 | C48 |
|----|-----|-----|-----|-----|-----|-----|-----|-----|-----|-----|-----|
| SN | 90 | 90 | 90 | 90 | 90 | 90 | 90 | 90 | 90 | 90 | 90 |
| AS | 10 | 9 | 8 | 7 | 6 | 5 | 9 | 8 | 7 | 6 | 5 |
| CO | | 1 | 2 | 3 | 4 | 5 | | | | | |
| CA | | | | | | | 1 | 2 | 3 | 4 | 5 |

|    | C49 | C50 | C51 | C52 | C53 | C54 | C56 | C57 | C58 | C59 | C60 |
|----|-----|-----|-----|-----|-----|-----|-----|-----|-----|-----|-----|
| SN | 90 | 90 | 90 | 90 | 90 | 90 | 90 | 90 | 90 | 90 | 90 |
| AS | 10 | 9 | 8 | 7 | 6 | 5 | 9 | 8 | 7 | 6 | 5 |
| CM | | 1 | 2 | 3 | 4 | 5 | | | | | |
| EP | | | | | | | 1 | 2 | 3 | 4 | 5 |

|    | C61 | C62 | C63 | C64 | C65 | C66 |
|----|-----|-----|-----|-----|-----|-----|
| SN | 90 | 90 | 90 | 90 | 90 | 90 |
| AS | 10 | 9 | 8 | 7 | 6 | 5 |
| GP | | 1 | 2 | 3 | 4 | 5 |

|    | C67 | C68 | C69 | C70 | C71 | C72 | C74 | C75 | C76 | C77 | C78 |
|----|-----|-----|-----|-----|-----|-----|-----|-----|-----|-----|-----|
| SN | 90 | 90 | 90 | 90 | 90 | 90 | 90 | 90 | 90 | 90 | 90 |
| CO | 10 | 9 | 8 | 7 | 6 | 5 | 9 | 8 | 7 | 6 | 5 |
| CA | | 1 | 2 | 3 | 4 | 5 | | | | | |
| CM | | | | | | | 1 | 2 | 3 | 4 | 5 |

|    | C79 | C80 | C81 | C82 | C83 | C84 | C86 | C87 | C88 | C89 | C90 |
|----|-----|-----|-----|-----|-----|-----|-----|-----|-----|-----|-----|
| SN | 90 | 90 | 90 | 90 | 90 | 90 | 90 | 90 | 90 | 90 | 90 |
| CM | 10 | 9 | 8 | 7 | 6 | 5 | 9 | 8 | 7 | 6 | 5 |
| EP | | 1 | 2 | 3 | 4 | 5 | | | | | |
| GP | | | | | | | 1 | 2 | 3 | 4 | 5 |

|    | C91 | C92 | C93 | C94 | C95 | C96 | C98 | C99 | C100 | C101 | C102 |
|----|-----|-----|-----|-----|-----|-----|-----|-----|------|------|------|
| SN | 90 | 90 | 90 | 90 | 90 | 90 | 90 | 90 | 90 | 90 | 90 |
| CA | 10 | 9 | 8 | 7 | 6 | 5 | 9 | 8 | 7 | 6 | 5 |
| CM | | 1 | 2 | 3 | 4 | 5 | | | | | |
| EP | | | | | | | 1 | 2 | 3 | 4 | 5 |

|    | C103 | C104 | C105 | C106 | C107 | C108 | C110 | C111 | C112 | C113 | C114 |
|----|------|------|------|------|------|------|------|------|------|------|------|
| SN | 90 | 90 | 90 | 90 | 90 | 90 | 90 | 90 | 90 | 90 | 90 |
| EP | 10 | 9 | 8 | 7 | 6 | 5 | 9 | 8 | 7 | 6 | 5 |
| GP | | 1 | 2 | 3 | 4 | 5 | | | | | |
| HP | | | | | | | 1 | 2 | 3 | 4 | 5 |

|    | C115 | C116 | C117 | C118 | C119 | C120 | C122 | C123 | C124 | C125 | C126 |
|----|------|------|------|------|------|------|------|------|------|------|------|
| SN | 90 | 90 | 90 | 90 | 90 | 90 | 90 | 90 | 90 | 90 | 90 |
| EP | 10 | 9 | 8 | 7 | 6 | 5 | 9 | 8 | 7 | 6 | 5 |

-continued

| KT | 1 | 2 | 3 | 4 | 5 | | | | | |
|---|---|---|---|---|---|---|---|---|---|---|
| LP | | | | | | 1 | 2 | 3 | 4 | 5 |

The above amounts provide exemplary useful amounts ±0.5% for amounts from 1-2%, ±0.5 or 1% for amounts from 3-5%, ±0.5, 1 or 2% for amounts from 6-10%, ±1, 2, 3, 4 or 5% for amounts from 70-90% (with the foregoing percentage ranges being of the total extract amount by weight).

In some embodiments, the solids from the extract(s) typically contribute amounts to the rinse from one of the following lower endpoints or from one of the following upper endpoints. The lower endpoints are 10, 15, 20, 25 and 30 weight percent. The upper endpoints are 15, 20, 25, 30, 35, 40 and 45 weight percent. The percent of such solids in the rinse can be, for example, approximately 30.0, 30.1, 30.2 and so in increments of 0.1 up to 40.0.

In some embodiments the herbal bioactive can be one or more flavonoids, isoflavonoids, tocopherols, polyphenols, or similar agents often found in herbal extracts.

Flavonoids can include, for example, flavonols or flavonolols [such as, without limitation, a rutoside: rutin (quercitin 3-O-rutino-side), quercitrin (quercetin 3-O-rhamno-side), isoquercitrin (quercetin 3-O-glucoside), diosmin (diosmetin 7.beta.-rutinoside), astragalin (kaempferol 3-O-glucoside), kaempferol 3-O-rutinoside, myricitrin (or myricetin 3-O-rhamnoside), robinin (or kaempferol 3-O-robinoside 7-rhamnoside), kaempferitrin (or kaempferol 3,7-O-dirhamnoside), nobiletin, tangeretin]. Or, flavonoids can include, for example, flavones [such as, without limitation, rhoifolin (or apigenin 7-O-neohesperido-side), luteolin 7-O-glucoside, scutellarin (or scutellarein 5-O-glucoside), pectolinarin (or pectolinarigenin 7-O-rutoside), galuteolin (or luteolin 5-O-glucoside), acaciin (or acacetin 7-O-rhamnoglucoside)]. Or, flavonoids can include, for example, flavanones [such as, without limitation, liquiritin (or liquiritin 4'-O-glucoside), naringin (or naringenin 7-O-neohesperido-side), hesperidin (or hesperetin 7-O-rut-inoside), eriodictin (or eridictiol 7-O-rhamnoside)].

Isoflavonoids can include, for example: formononetin 7-O-glucoside (or ononin), afromosin 7-O-glucoside (or wistin), genistein (or genistein 7-O-glucoside), daidzin, glycitin, genistein 6-O-malonylglucoside, daidzein 6-O-malonylglucoside, genistein 6-O-acetyl-glucoside, iridin (or irigenin 7-O-glucoside), irisolone, tectoridin (or tectorigenin 7-O-glucoside) or shekanin.

If any one of these specific bioactive agents is included in the rinse it can be used in an amount corresponding to the amount found in one of the above-described extracts.

2. Polymer

The rinses of the invention contain, in certain embodiments, polymer selected to form a film on mucosal tissue and entrap an amount of herbal extract. Any polymer that coats the appropriate mucosal tissue can be used. Some illustrative examples include crosslinked polyacrylic acid-moiety-containing polymers (which can be esterified) (e.g., Carbopol™), carboxymethyl cellulose salts (e.g., Na—CMC), hydroxypropylmethylcellulose (Methocel™), hyaluronic acid, alginate gum, chitosan, pectin, locust bean gum, xantan gum, acacia gum, the foregoing crosslinked, and the like. The polymer can be water-swellable or water dispersible. Other polyanionic polymers, such as those described in U.S. Pat. No. 4,615,697, can be used. Or, polycationic polymers (such as chitosan) can be used.

Polymers can include or consist of polyethylene/polypropylene block copolymers (poloxamers). Appropriately selected, and in appropriate amounts, such polymers can provide the thermal annealing discussed below.

Depending on the embodiment, the film formed with the rinse may entrap a range of percentages of the herbal extract in the rinse. Thus, the liquid portion (i.e., the non-coated portion) of the rinse can deliver medicament during the rinse and possibly for a period thereafter, while the coated portion can provide longer term delivery. The localization of medicament at or near the affected site counterbalances any reductions in amount during the sustained delivery portion of an administration.

a. Mucoadhesive

In certain embodiments the polymer(s), relative amounts, and concentrations are selected to provide a film that is mucoadhesive. The term mucoadhesive, as used herein, is a material that adheres to a mucosal tissue surface in-vivo and/or in-vitro. Such adhesion will adherently localize the dosage form onto the mucus membrane and in certain embodiments requires the application of a force of at least about 50 dynes/$cm^2$ to separate the mucoadhesive material from the mucus membrane.

Appropriately selected, the polymer composition is, in certain embodiments, less adhesive on teeth.

Crosslinked polyacrylic acid-moiety-containing polymers and/or polysaccharide gums (e.g. chitosan) can be used to achieve such mucoadhesion.

b. Thermal Annealing Polymer

In certain embodiments, the polymer comprise polymers that reversible gel at temperatures approaching 35° C., but are water dispersible at temperatures of about 25° C. or less. Thus, film-forming at the mucosal surface can be increased, as a more liquid rinse can be applied, and gel-forming is accentuated at or near the warmer surfaces of tissue.

Such thermal annealing is provided by, for example, polyethylene/polypropylene block copolymers, such as polyethylene-polypropylene-polyethylene triblock copolymers. Examples can include the Poloxamer (i.e., Pluronic™) polymers available from BASF, such as Poloxamer 407, 338, 237, 188, and the like, provided in the polymer component (as all or a part thereof).

3. Rinse

In certain embodiments, the rinse comprises an effective amount of an appropriate composition of herbal bioactive comprising active(s) of one or more of *Sambucus nigra, Centella asiatica* or *Echinacea purpurea*, and an antimicrobially effective amount of a quaternary ammonium compound that is surface active.

4. Antimicrobial Agents

In certain embodiments the rinse includes antimicrobial agents in amounts effective to reduce the growth of one or more gingivitis-associated microbes. Antimicrobial agents can be surface active quaternary ammonium compounds, chlorohexidine, zinc salt(s) (e.g., chloride), fluoride salt(s) (e.g., Na/Sn fluoride), triclosan, benzydamine, chlorobutanol, chlorothymol, thymol, methyl salicylate, menthol, alkyl sulfate salt(s) (e.g., sodium lauryl sulfate), peroxides (e.g., hydrogen peroxide), and the like In certain embodiments the rinse includes an antimicrobially effective amount of a quaternary ammonium compound that is surface active. Such antimicrobial surfactants can include, for example, 1-alkylpyridinium salts, where alkyl is C8-C36 (or C8-C20, or C10-C20), and wherein the carbon ring members can be substituted with up to two C1-C7 alkyl groups. For example, the rinse can include cetylpyridinium chloride.

In some embodiments, the quaternary ammonium compound(s) typically contribute amounts to the rinse from one of the following lower endpoints or from one of the following upper endpoints. The lower endpoints are 0.01, 0.02, 0.03, 0.04 and 0.05 weight percent. The upper endpoints are 5, 4, 3, 2, 1, 0.9, 0.8, 0.7, 0.6, 0.5, 0.25, 0.15, 0.14, 0.13, 0.12, 0.11, 0.10, 0.09 and 0.08 weight percent.

5. Penetrants

Plasticizers, penetration enhancers, flavoring agents, preservatives, coloring agents, surfactants and the like can be included in the rinse. Plasticizers will generally modify the feel, softness, flexibility of the film. Penetration enhancers may, in some cases, act as plasticizers. Examples of plasticizers include, without limitation, glycerol, propylene glycol, sorbitol, fatty acid esters (such as glyceryl oleate), and the like. Examples of penetration enhancers include, without limitation, fatty acid esters, fatty alcohol ethers, PEG-[C10-C30]alkyl, N-lauroyl sacrcosine, sorbitan monolaurate, stearyl methacrylate, N-Dodecylazacycloheptan-2-one, N-dodecyl-2-pyrrolidinone, N-dodecyl-2-piperidinone, 2-(1-nonyl)-1,3-dioxolane, N-(2-methoxymethyl) dodecylamine, N-dodecylethanolamine, N-dodecyl-N-(2-methoxymethyl)acetamide, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 2-dodecyl-2-oxo-1-pyrrolidineacetic acid, 1-azacylioheptan-2-one-dodecylacetic acid, and the like.

In some embodiments, the plasticizers can contribute amounts to the rinse from one of the following lower endpoints or from one of the following upper endpoints. The lower endpoints are 10, 15, 20, 25 and 30 weight percent. The upper endpoints are 15, 20, 25, 30, 35, 40 and 45 weight percent. The percent of plasticizers in the rinse can be, for example, approximately 30.0, 30.1, 30.2 and so in increments of 0.1 up to 40.0.

6. Alcohol-Free Rinses

In certain embodiments, the rinse lacks propyl or ethyl alcohols in amounts that are antimicrobially effective.

7. Illustrative Indications: Treatment Parameters

Indications treated with the methods and devices of the invention include any indication of mucosal tissue, or tissue sufficiently adjacent to mucosal tissue, treatable with the plant extracts and/or described antimicrobial agents. For example, oral indications and microbial indications (such as microbial lesions) can be treated with the methods and devices.

Oral indications appropriate for treatment with the invention include, without limitation, periodontal disease, gingivitis, aphthous ulceration (e.g., canker sores, recurrent aphthous stomatitis, recurrent ulcerative stomatitis), mechanical trauma, thermal trauma, the oral lesions, dry mouth (xerostomia), mucositis or eruptions of lichen planus, bullous pemphigoid, pemphigus vulgaris, dermatitis herpetiformis or angular chelitis, recurrent herpes, other microbial (including viral) eruptions of the oral mucosa, lesions (including the foregoing and such as mucositis) secondary to chemotherapy or radiation treatment, lesions resulting from trauma (including chemical or other burns), lesions secondary to systemic disease, lesions resulting from autoimmune disease, lesions with idiopathic causes, or the like. The herbal component of the rinse typically includes components selected to reduce inflammation. In certain embodiments, the herbal component is effective to reduce matrix metalloprotease(s) expressed at or near the mucosal membrane, and/or to reduce cytokine(s) expressed at or near the mucosal membrane.

In the case of mucositis secondary to chemotherapy or radiation treatment, the rinse can be administered after the primary chemotherapy treatment, but before symptoms of mucositis are apparent.

In many embodiments, the treated tissue is in the mouth. In other embodiments, the treatment tissue is at or adjacent to other mucosal tissue, such as nasal, anal, vaginal, and the like.

8. Solid Dosage Forms for Use with the Rinse

In certain embodiments, the rinse is administered in conjunction with another administration form, such as a film, patch or mucoadhesive solid dosage form. This solid dosage form can be applied before, concurrently, or after administration of the rinse. The solid forms can help deliver medicament to more severely affected, or more mechanically accessible tissue, while the rinse delivers medicament elsewhere. The medicament in the solid form can be the same or different from that of the rinse. However, herbal extracts and extract mixtures as described above are usefully employed. Similarly, quaternary amine surfactants are usefully employed. For example, the dosage described in WO 02/094300 and PCT/US05/42348 can be employed. Or, the film described in the an application, filed Jun. 20, 2007, titled "Anti-Inflammatory Dissolvable Film", Ser. No. 11/765,587, can be employed.

9. Antiinflamatory Agents

In certain embodiments, the rinse further comprising antiinflammatory agent(s), such as steroidal or nonsteroidal anti-inflammatory agents. Steroidal anti-inflammatory agents, include but are not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Other anti-inflammatory agents useful in the compositions include the nonsteroidal anti-inflammatory agents. The variety of compounds encompassed by this group are well-known to those skilled in the art. For detailed disclosure of the chemical structure, synthesis, side effects, etc. of non-steroidal anti-inflammatory agents, reference can be had to standard texts, including Anti-inflammatory and Anti-Rheumatic Drugs, K. D. Rainsford, Vol. I-III, CRC Press, Boca Raton, (1985), and Anti-inflammatory Agents, Chemistry and Pharmacology 1, R. A. Scherrer, et al., Academic Press, New York (1974).

Specific non-steroidal anti-inflammatory agents useful in the composition invention include, but are not limited to: 1)

the oxicams, such as piroxicam, isoxicam, tenoxicam, sudoxicam, and CP-14,304; 2) the salicylates, such as aspirin, disalcid, benorylate, trilisate, safapryn, solprin, diflunisal, and fendosal; 3) the acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; 4) the fenamates, such as mefenamic, meclofenamic, flufenamic, niflumic, and tolfenamic acids; 5) the propionic acid derivatives, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; 6) the pyrazoles, such as phenylbutazone, oxyphenbutazone, feprazone, azapropazone, and trimethazone; and mixtures of the foregoing.

Mixtures of these steroid and/or non-steroidal anti-inflammatory agents can be employed, as well as the pharmologically acceptable salts and esters of these agents. For example, etofenamate, a flufenamic acid derivative, is particularly useful for topical application.

The following examples further illustrate the present invention, but of course, should not be construed as in any way limiting its scope.

Definitions

The following terms shall have, for the purposes of this application, the respective meanings set forth below.

Effective Amount

To treat the indications of the invention, an effective amount of a pharmaceutical compound will be recognized by clinicians but includes an amount effective to treat, reduce, alleviate, ameliorate, eliminate or prevent one or more symptoms of the disease sought to be treated or the condition sought to be avoided or treated, or to otherwise produce a clinically recognizable favorable change in the pathology of the disease or condition. Thus, an effective amount can be, for example, an amount that reduces the severity or duration of oral lesions, ulcerations, bleeding, irritation, swelling, erythema, or the like.

Microbial Infections

Microbial infections include, without limitation, bacterial, mycobacterial, fungal and viral infections.

Treatment

"Treatment" means the management and care of a patient for the purpose of combating a disease, disorder or condition. The term is intended to include the delaying of the progression of the disease, disorder or condition, the alleviation, amelioration or relief of symptoms and complications, and/or the cure or elimination of the disease, disorder or condition. The animal to be treated can be a mammal, in particular a human being.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of treating or ameliorating an indication of mucosal or adjacent tissue comprising periodically applying to oral mucosa at or adjacent to disease affected tissue a formulation comprising
    an anti-gingivitis effective amount of herbal extracts including *Sambucus nigra, Centella asiatica* and *Echinacea purpurea* defining a weight amount of plant extract solids in the formulation, wherein *Sambucus nigra* extract is more than 50% to 90% by weight of the plant extract solids and *Centella asiatica* is 1% to less than 50% by weight of the plant extract solids,
    a plasticizer in an amount from 10 to 45% by weight of the formulation, and
    an antimicrobially effective amount of a surfactant that is a 1-alkylpyridinium salt, where alkyl is C8-C36, the surfactant present in an amount from 0.01 to 2% of the formulation by weight.

2. The method of claim 1, further comprising applying to a portion of the mucosa a film, patch or an adhesive solid formulation comprising a composition of herbal bioactive comprising active(s) of one or more of *Sambucus nigra, Centella asiatica* or *Echinacea purpurea*.

3. The method of claim 1, wherein the 1-alkylpyridinium salt is a cetylpyridinium salt.

4. The method of claim 1, wherein *Sambucus nigra* extract comprises 60 to 99% by weight of plant extract solids in the formulation.

5. The method of claim 1, wherein the surfactant is present in an amount from 0.01 to 1% of the formulation by weight.

6. The method of claim 4, wherein *Centella asiatica* extract comprises 5 to 40% by weight of plant extract solids in the formulation.

7. The method of claim 6, wherein the surfactant is present in an amount from 0.01 to 1% of the formulation by weight.

8. The method of claim 6, wherein *Echinacea purpurea* extract comprises 1 to 20% by weight of plant extract solids in the formulation.

9. The method of claim 1, wherein *Centella asiatica* extract comprises 5 to 40% by weight of plant extract solids in the formulation.

10. The method of claim 1, wherein *Echinacea purpurea* extract comprises 1 to 20% by weight of plant extract solids in the formulation.

11. The method of claim 1, wherein the formulation is essentially free of added synthetic polymers.

\* \* \* \* \*